(12) United States Patent
Helmer et al.

(10) Patent No.: US 8,900,203 B2
(45) Date of Patent: Dec. 2, 2014

(54) DRUG DELIVERY DEVICE WITH CLEARANCE COMPENSATION MEANS

(75) Inventors: Michael Helmer, Frankfurt am Main (DE); Claudia Matthias, Frankfurt am Main (DE); Leo Zeimetz, Büttelborn (DE); Reza Shahbazfar, Wiesbaden (DE); Benjamin Schaefer, Bischoffen (DE); Carsten Mosebach, Mainz (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 289 days.

(21) Appl. No.: 13/500,418

(22) PCT Filed: Oct. 8, 2010

(86) PCT No.: PCT/EP2010/065095
§ 371 (c)(1),
(2), (4) Date: Sep. 17, 2012

(87) PCT Pub. No.: WO2011/042538
PCT Pub. Date: Apr. 14, 2011

(65) Prior Publication Data
US 2012/0330244 A1    Dec. 27, 2012

(30) Foreign Application Priority Data
Oct. 8, 2009    (EP) .................................... 09172506

(51) Int. Cl.
*A61M 5/00*    (2006.01)
*A61M 5/24*    (2006.01)
*A61M 5/31*    (2006.01)
*A61M 5/315*    (2006.01)

(52) U.S. Cl.
CPC ............... *A61M 5/24* (2013.01); *A61M 5/3129* (2013.01); *A61M 5/3146* (2013.01); *A61M 5/31525* (2013.01); *A61M 5/31533* (2013.01); *A61M 2005/2407* (2013.01); *A61M 2005/2488* (2013.01); *A61M 2005/2492* (2013.01); *A61M 2207/00* (2013.01)
USPC ......................................... 604/208; 604/207

(58) Field of Classification Search
CPC ... A61M 5/24; A61M 5/31525; A61M 5/315; A61M 5/31533
USPC ................................................... 604/207, 208
See application file for complete search history.

(56) References Cited

U.S. PATENT DOCUMENTS 5,688,251 A * 11/1997 Chanoch ....................... 604/208
2005/0049551 A1    3/2005 Kirchhofer

FOREIGN PATENT DOCUMENTS

| EP | 0893133 | * | 1/1999 |
| EP | 1911479 | | 4/2008 |
| JP | 52-119787 U1 | | 9/1977 |
| WO | 97/10864 | | 3/1997 |
| WO | 2009/095332 | | 8/2009 |

OTHER PUBLICATIONS

European Search Report for European App. No. 09172506, completed Mar. 23, 2010.
International Search Report for International App. No. PCT/EP2010/065095, completed Jan. 12, 2011.
International Preliminary Report on Patentability for International App. No. PCT/EP2010/065095, completed Sep. 26, 2011.

* cited by examiner

*Primary Examiner* — Kevin C Sirmons
*Assistant Examiner* — Deanna K Hall
(74) *Attorney, Agent, or Firm* — McDonnell Boehnen Hulbert & Berghoff LLP

(57) ABSTRACT

The present invention relates to a drug delivery device for dispensing of a predefined dose of a medicinal product, comprising: a housing, a cartridge holder adapted to receive a cartridge containing the medicinal product to be dispensed, the cartridge holder being connectable to the housing, a drive mechanism to be operably engaged with the cartridge for setting and/or dispensing of a predefined dose of the medicinal product, wherein the drive mechanism is axially slidingly supported in the housing for compensating axial clearance between the drive mechanism and the cartridge and wherein the drive mechanism is axially fixable relative to the housing.

11 Claims, 3 Drawing Sheets

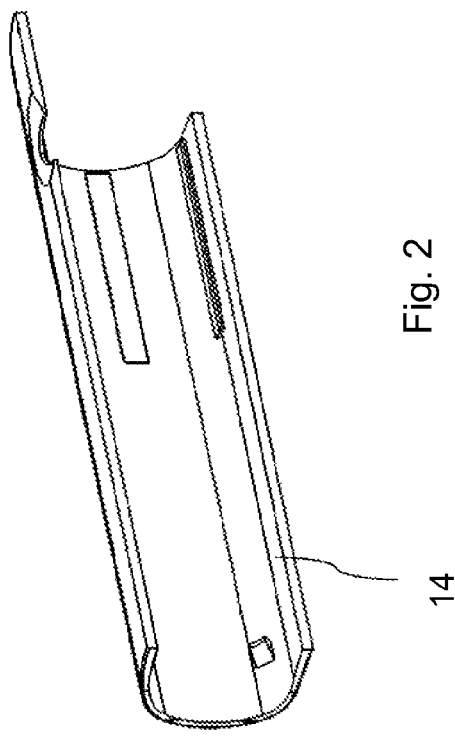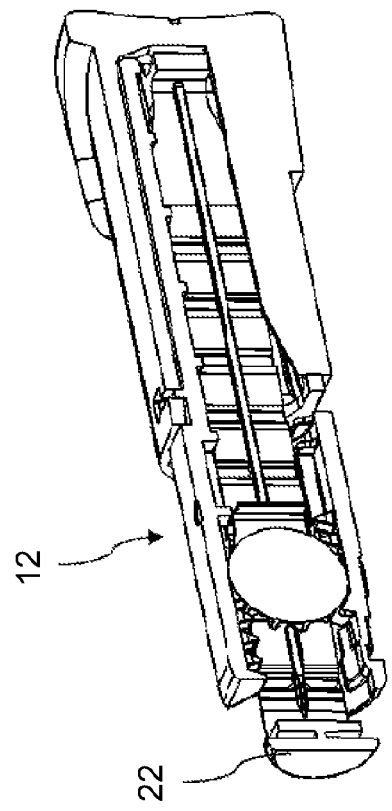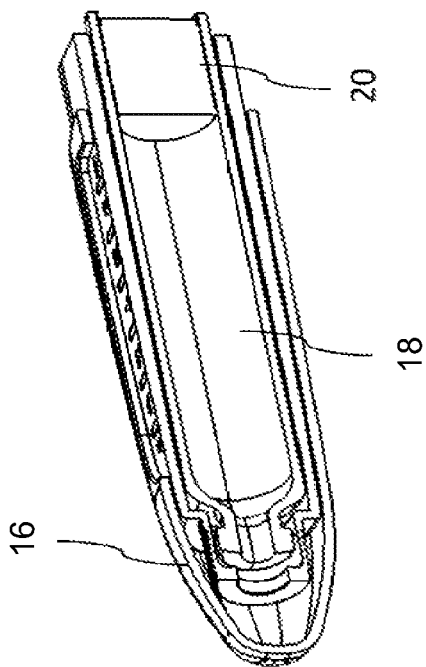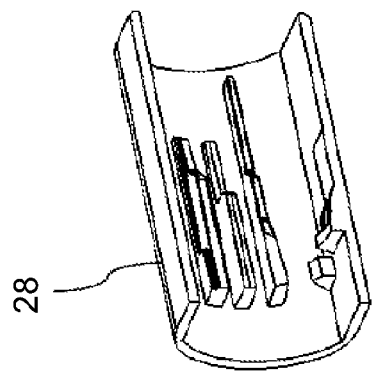

DRUG DELIVERY DEVICE WITH CLEARANCE COMPENSATION MEANS

CROSS REFERENCE TO RELATED APPLICATIONS

The present application is a U.S. National Phase Application pursuant to 35 U.S.C. §371 of International Application No. PCT/EP2010/065095 filed Oct. 8, 2010, which claims priority to European Patent Application No. 09172506.9 filed on Oct. 8, 2009. The entire disclosure contents of these applications are herewith incorporated by reference into the present application.

FIELD OF THE INVENTION

The present invention relates to a drive mechanism for a drug delivery device that allows a user to select single or multiple doses of an injectable medicinal product and to dispense the set dose of the product and to apply said product to a patient, preferably by injection. In particular, the present invention relates to such devices, which are handled by the patients themselves.

BACKGROUND

Drug delivery devices allowing for multiple dosing of a required dosage of a liquid medicinal product, such as liquid drugs, and further providing administration of the liquid to a patient, are as such well-known in the art. Generally, such devices have substantially the same purpose as that of an ordinary syringe.

Drug delivery devices of this kind have to meet a number of user specific requirements. For instance in case of those with diabetes, many users will be physically infirm and may also have impaired vision. Therefore, these devices need to be robust in construction, yet easy to use, both in terms of the manipulation of the parts and understanding by a user of its operation. Further, the dose setting must be easy and unambiguous and where the device is to be disposable rather than reducible, the device should be inexpensive to manufacture and easy to dispose. In order to meet these requirements, the number of parts and steps required to assemble the device and an overall number of material types the device is made from have to be kept to a minimum.

Typically, the medicinal product to be administered is provided in a cartridge that has a moveable piston or bung mechanically interacting with a piston rod of a drive mechanism of the drug delivery device. By applying thrust to the piston in distal direction, a predefined amount of the medicinal fluid is expelled from the cartridge.

Due to inevitable manufacturing tolerances there may for instance persist axial clearance between a cartridge's piston and the piston rod. Typically, prior to a primary use of the device, an end-user has to conduct a so-called priming of the drive mechanism in order to ensure, that already with an initial dose setting and a first subsequent dose dispensing step, an accurate amount of the medicinal product is disposed in a predefined way.

Since a self-administering user might be physically infirm, it is desirable to simplify or even to eliminate the need for such a user-conductible priming procedure.

Document EP 1 911 479 A1 discloses for instance a dose dispensing device, wherein a piston and a piston rod are electromagnetically or magnetically coupled, and wherein the piston and piston rod comprise a magnetic effect generating member.

Since the generation of an electromagnetic field requires a supply of electric energy, such a solution is generally not applicable to drug delivery devices of pen-injector type.

Insofar, known solutions feature the common drawback, that for elimination of axial clearance between piston rod and piston, the piston rod has to be axially shifted by its associated drive mechanism. Axial clearance- and backslash elimination implies to bring the piston rod in direct abutment position with a cartridge's piston. Such axial displacement of the piston rod for the purpose of clearance elimination is regarded as disadvantageous, because it typically involves a respective actuation of dose setting or dose dispensing means by the user.

It is therefore an object of the present invention to provide a drive mechanism for a drug delivery device featuring improved and facilitated clearance and manufacturing tolerance elimination. It is a further object of the invention to redundantize a priming procedure to be conducted by the end user. The invention further focuses on improvements related to patient safety and intends to simplify the general device handling. It is a further object of the invention, to provide a drive mechanism for a drug delivery device with clearance eliminating means being inexpensive to produce and being easy to assemble. Finally, it is an object of the invention to provide a method of eliminating clearance in a drive mechanism of a drug delivery device.

SUMMARY

The present invention provides a drug delivery device for dispensing of a predefined dose of a medicinal product. The device comprises a housing, a cartridge holder to be interconnected with the housing and a drive mechanism which is to be operably engaged with the cartridge for setting and/or dispensing of said predefined dose. The cartridge holder is further adapted to receive a cartridge that contains the medicinal product to be dispensed. Said cartridge may comprise a vial, carpule or ampoule and may be filled with a liquid drug, such as insulin or heparin. The drug delivery device is preferably designed as pen-type injector. Hence, the cartridge is to be coupled with an injection needle, cannula or the like in a fluid-transferring way.

While the cartridge is to be placed in the cartridge holder, the drive mechanism to be operably engaged with the cartridge, in particular with its slidingly supported piston, is arranged inside the housing. The coupling of the drive mechanism and the housing is such, that the drive mechanism is axially slidingly supported in the housing within a certain range. By means of such an axially adjustable pre-assembly of drive mechanism and housing, axial clearance between the dose dispensing mechanism and the cartridge can be compensated, in particular during the final assembly of the drug delivery device.

Further, when a final assembly position, characterized by mutual engagement of housing and cartridge holder, has been reached, the drive mechanism is to be axially fixed and immobilized relative to the housing. Hence, the axially slidingly support of the drive mechanism exclusively serves to compensate for manufacturing and assembly tolerances and/or serves to eliminate respective clearance.

In effect, the axially sliding support of the drive mechanism allows for an assembly of the cartridge inside the cartridge holder as well as for pre-assembling of a sliding arrangement of the drive mechanism inside the housing. At a certain stage during assembly of cartridge holder and housing, the drive mechanism operably engages with the cartridge's piston.

Typically, the piston rod abuts against a piston of the cartridge.

When a mutual abutment configuration of drive mechanism and cartridge has been reached, in the further course of mutual assembly of housing and cartridge holder, the drive mechanism and the housing may become subject to a relative axial displacement. However, as soon as the final assembly configuration has been reached, the operable engagement of a drive mechanism and cartridge is substantially free of clearance. By way of a subsequent immobilizing of the drive mechanism relative to the housing, said clearance-free configuration can be sustained and the drug delivery device is prepared for initial dose setting and dispensing without the necessity of initially performing a clearance-compensating priming procedure.

A mutual locking in position of drive mechanism and housing can be established irrespective of the relative distance between piston rod and housing. As soon as an abutment position with the piston has been reached, the piston rod itself may remain stationary with respect to the cartridge but may be subject to axial displacement relative to the housing.

The drug delivery device further comprises a guiding element which is axially coupled or even axially connected to the drive mechanism. Further, said guiding element is slidingly received in the housing. The guiding element serves as a kind of adapter, which is on the one hand operably engaged and fixed to the drive mechanism. On the other hand, said guiding element provides a clearance-compensating axial displacement of drive mechanism and housing. By way of the guiding element, the drive mechanism can be axially shifted with respect to the housing in its entirety. This way, axial clearance can be compensated without the necessity of activating or otherwise manipulating the drive mechanism and/or any of its components. The drive mechanism itself and its components can therefore remain completely unaffected or untouched during a clearance compensating procedure. A clearance elimination procedure therefore limits to an axial displacement of the guiding element relative to the housing of the drug delivery device.

In a further preferred embodiment, the guiding element comprises a sleeve, preferably a substantially cylindrical sleeve, which is adapted to receive the drive mechanism. The sleeve itself is axially displaceably supported in the housing. In this way, the cylindrical sleeve provides axial clearance elimination, typically between the piston of the cartridge and the piston rod or plunger of the drive mechanism, which is adapted to exert distally directed thrust to the cartridge's piston.

According to a further preferred embodiment, the guiding element and the housing are mutually infinitely adjustable. In this way, the relative axial displacement of guiding element and housing is particularly smooth. A smooth-running relative axial displacement of guiding element and housing is further beneficial for the final assembly of housing and cartridge holder. In this way, an unintentional axial displacement of the cartridge's piston in the course of a final assembly procedure can be effectively precluded. Axial thrust which may otherwise act on the piston during final assembly predominately discharges in a relative motion of guiding element and housing.

In a further, alternative embodiment, the guiding element and the housing are mutually engageable by means of a positive locking means. Positive locking of guiding element and housing can for instance be achieved by providing the guiding element and the housing with mutually corresponding detent elements, such like cogged or geared inner and outer cylindrical walls. In this context, it is even conceivable, to configure the guiding element and the housing in such a way, that guiding element and housing are unidirectionally axially displaceable.

Typically, positive locking means of guiding element and housing are designed to allow the housing to be displaced in distal direction relative to the guiding element; that is towards the cartridge holder. In other words, a distally directed displacement of the guiding element relative to the housing is to be blocked by said locking means.

In a further embodiment, the guiding element and the housing are mutually bonded or welded, e.g. by means of an appropriate adhesive or by means of deposition of energy in a region, where guiding element and housing overlap in radial direction. Energy deposition for the purpose of mutually welding the guiding element and the housing can for instance be provided by electromagnetic radiation, e.g. by laser irradiation of the respective portions.

According to a further embodiment, a deformable adhesive can be disposed at the outer surface of the guiding element or at an inner surface of the housing. For this purpose, inner and outer surface portions of the guiding element and the housing may comprise at least one receptacle. The interlocking of the guiding element and the housing can then achieved in a second step by curing of said adhesive. The curing of said adhesive and hence the immobilization and mutual interlocking of guiding element and housing can be supported or triggered by energy deposition, e.g. by means of irradiation with electromagnetic radiation or by application of thermal energy.

Generally, and according to another preferred embodiment, the guiding element and the housing are adhesively connected, mutually bonded and/or mutually welded. Such non-positive or force-fitting coupling of housing and guiding element is to be preferred in connection with mutual infinitely adjustment of housing and guiding element.

Preferably, the mutual interconnection of housing and guiding element is designed as a laser-welded connection. For this purpose, the housing is at least partially transparent for a particular laser radiation wavelength. In order to achieve a sufficient welding effect, the guiding element comprises a material being adapted to at least partially absorb said laser radiation. In this way, a sufficient amount of laser radiation and thermal energy can be deposited at the interface of guiding element and housing. In effect, the guiding element at least partially melts on, so that the housing and the guiding element can be joined by casting.

In further typical and independent embodiments, the cartridge holder and the housing are mutually coupled in axial direction. Preferably, cartridge holder and housing can be coupled by positive locking means, which may even allow disassembling of housing and cartridge holder, e.g. for replacing of a used cartridge. However, such disassembling is only preferred in conjunction with embodiments, where the guiding element and the housing are detachably interconnected.

According to a further preferred embodiment of the invention, the guiding element provides exclusive axial and mechanical coupling of the drive mechanism and the housing. In this way, any user induced relative thrust or force between housing and drive mechanism is almost entirely transferred by the guiding element.

In still another aspect, the drug delivery device comprising a cartridge filled with the medicinal product. This way, when commercially distributed, the drug delivery device is already equipped with a cartridge filled with the medicinal product or medicament to be disposed by the drug delivery device.

Hence, the device can be delivered in a configuration in which it is ready for use.

According to a further independent aspect, the invention also provides a method of eliminating axial clearance between a cartridge and a drive mechanism of a drug delivery device. Said method of clearance elimination is preferably performed in the course of a final assembly of the drug delivery device. In a first step, the cartridge is disposed in a cartridge holder and the drive mechanism is disposed inside a housing component, wherein the drive mechanism remains axially slidingly supported relative to the housing within a certain axial range.

In a second step and during assembly of cartridge holder and housing, the drive mechanism becomes subject to an axial displacement with respect to the housing in response of the drive mechanism becoming operably engaged with the cartridge. Due to the relative axial displacement of drive mechanism and housing as an effect of mutual abutment of the drive mechanism's piston rod and a cartridge's piston, axial clearance between said piston rod and piston can be effectively eliminated.

Finally, in a third step, and after assembly of cartridge holder and housing, the drive mechanism is axially fixed and immobilized with respect to the housing. Since housing and cartridge holder are directly interconnected, the drive mechanism becomes also immobilized and axially fixed with respect to a cartridge holder.

The term "medicament" or "medicinal product", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(w-carboxyheptadecanoyl)-des(B30) human insulin and B29-N-(w-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be apparent to those skilled in the pertinent art, that various modifications and variations can be made to the present invention without departing from the spirit and scope of the invention. Further, it is to be noted, that any reference signed used in the appended claims are not to be construed as limiting the scope of the present invention.

BRIEF DESCRIPTION OF THE DRAWINGS

FIG. 2 depicts a partially intersected and perspective illustration of the cartridge holder and the housing, FIG. 3 perspectively illustrates guiding element and drive mechanism

DETAILED DESCRIPTION

Figure 1:
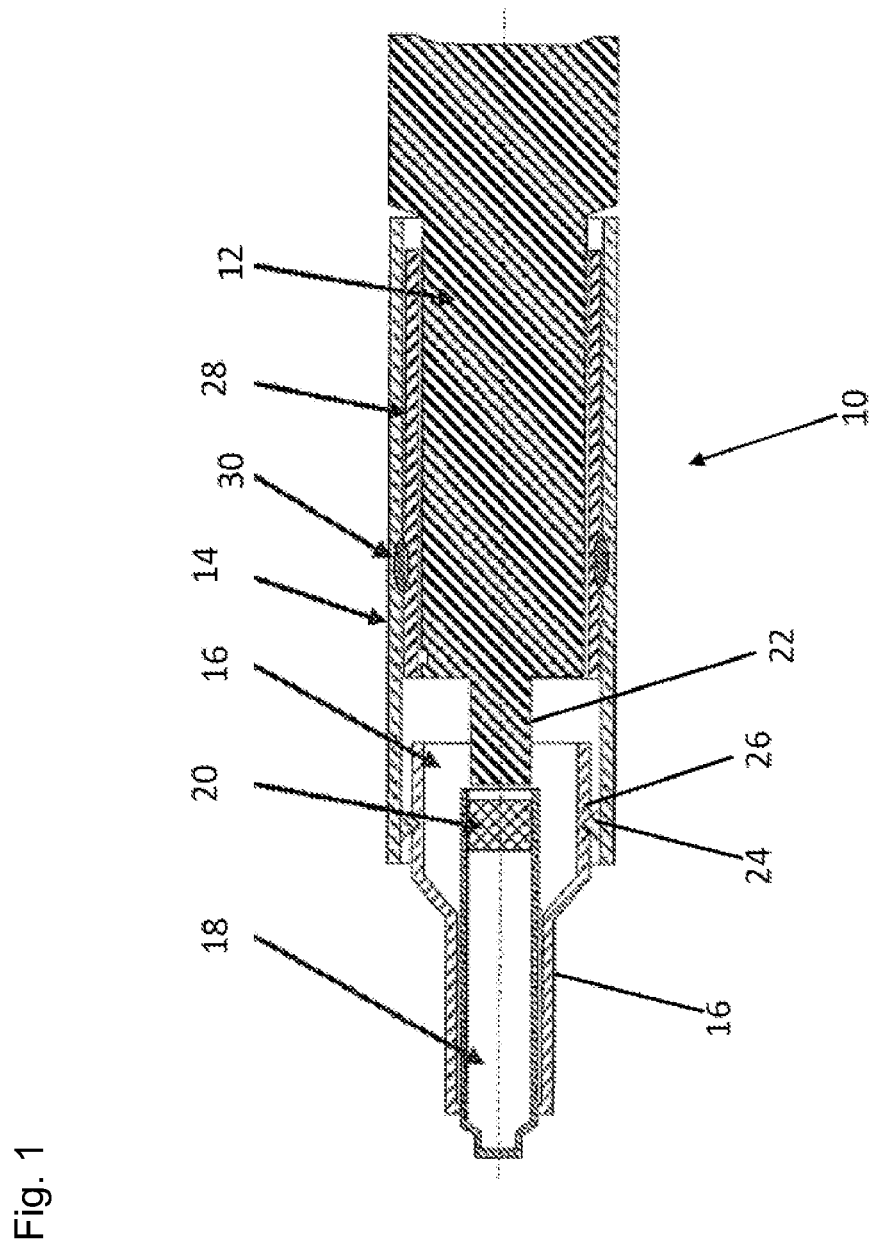
FIG. 1 shows a cross-sectional illustration of the drug delivery device in final assembly configuration.

In the schematic illustrations of FIGS. 1 to 4, the drug delivery device 10 comprises a cylindrical housing component 14, which at its distal end section is interconnected with a cartridge holder 16. A cartridge 18 filled with a medicinal product to be dispensed is disposed in the cartridge holder 16. The cartridge 18 comprises a piston 20 at its proximal end section to be operably engaged with a piston rod or plunger 22 of a drive mechanism 12. A mechanical coupling of the drive mechanism 12 and the housing 14 is provided by a sleeve-like guiding element 28. Even though not particularly illustrated in the Figures, the guiding element 28 is axially fixed and coupled with the drive mechanism 12. The guiding element 28 is axially slidingly supported in the housing 14. The guiding element 28 and the drive mechanism 12 may be positively engaged at least with respect to the axial direction of the drug delivery device. By way of the guiding element, the drive mechanism 12 is slidably disposed relative to the housing 14 in its entirety.

Axial clearance between the piston 20 and the piston rod 22 is preferably eliminated during and in the course of a final assembly of cartridge holder 16 and housing 14. Typically, final assembly of the drug delivery device 10 comprises mutual assembly and mutual interlocking of first and second sub-assemblies. In this context, a first sub-assembly comprises the cartridge holder 16 and its pre-assembled cartridge 18. The second pre-assembly comprises the housing 14 and the drive mechanism 12 slidingly supported therein.

During final assembly, wherein first and second sub-assemblies, the cartridge holder 16 and the housing 14 are mutually interconnected, the piston rod 22 with its distal end face or thrust piece abuts against a proximal end face of the cartridge's 18 piston 20. In the further course of the assembly procedure, the guiding element 18 together with its drive mechanism 12 remains axially fixed with respect to the cartridge holder 16 and its cartridge 18 due to said abutment of piston rod 22 and piston 20. The illustrated positive locking in form of a radially protruding peg and an annular groove 26 are only exemplary. An interconnection of housing 14 and cartridge 16 can be provided in any other suitable way, e.g. also by means of a threaded engagement or by means of an adhesive.

Figure 4:
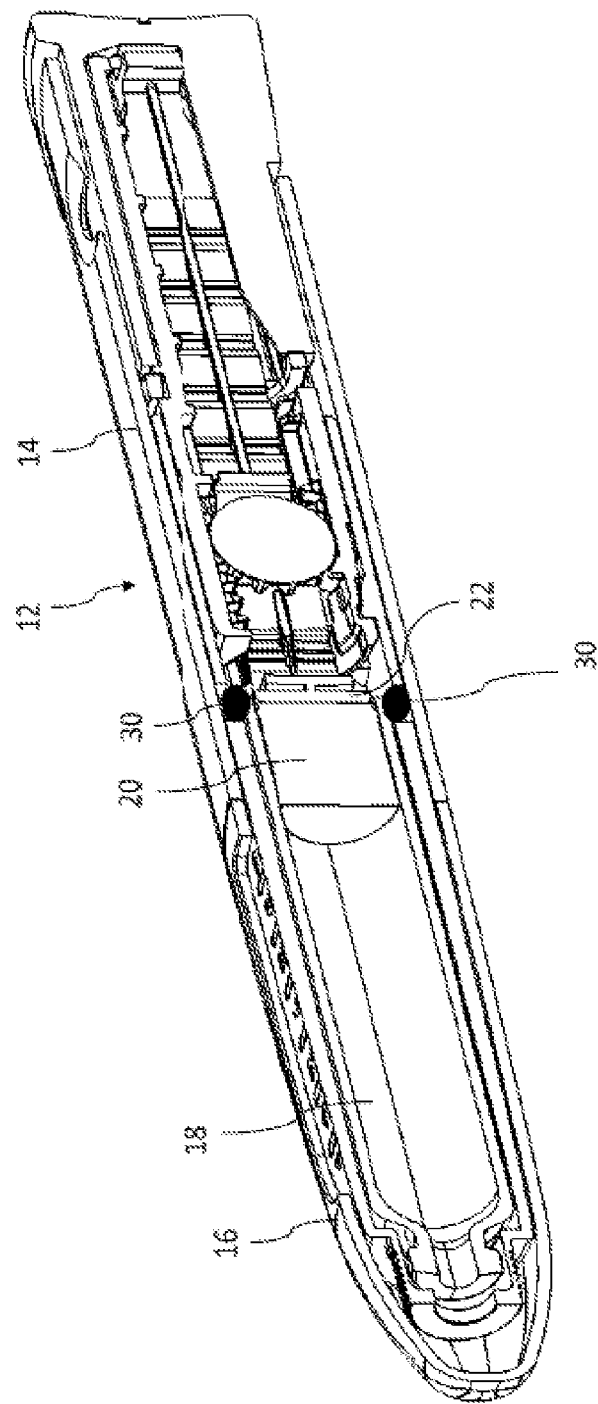
FIG. 4 shows the components according to FIGS. 2 and 3 in final assembly configuration.

In effect, the housing 14 experiences axial displacement relative to the guiding element 28 until its final assembly configuration with respect to the cartridge holder 16 has been reached. After having reached the final assembly configuration as depicted in FIGS. 1 and 4, guiding element 28 and housing 14 are mutually immobilized, by means of a laser-welding procedure. For this purpose, the housing 14 and/or the guiding element 28 are subject to thermal energy deposition in the area of a weld spot 30.

The welding of guiding element 28 and housing 14 may comprise numerous welded spots 30. It is even conceivable, to implement a rim- or ring-like mutual welding of housing 14 and guiding element 28.

Further, it is conceivable, to provide and to dispose a laser welding material in an annular groove of the guiding element 28 and/or the housing 14. The laser welding material can for instance be selected according to its radiation absorption properties, whereas the material of both, guiding element 28 and housing 14 can be substantially transparent for the laser radiation used for the laser welding process.

The invention claimed is:

1. A drug delivery device for dispensing of a predefined dose of a medicinal product, comprising:
   a housing;
   a cartridge holder configured to connect to the housing and to receive a cartridge containing the medicinal product to be dispensed;
   a drive mechanism configured for operable engagement with the cartridge for setting and/or dispensing of a predefined dose of the medicinal product, where the drive mechanism is further configured in its entirety to be slidable axially relative to the housing and axially fixable relative to the housing after engagement with the cartridge; and
   a guiding element axially coupled to the drive mechanism and slidably received within the housing such that the entire drive mechanism and the guiding element are both slidable axially within and relative to the housing for compensating for axial clearance between the drive mechanism and the cartridge.

2. The drug delivery device according to claim 1, wherein the guiding element comprises a sleeve adapted to receive the drive mechanism, the sleeve being axially displaceably supported in the housing for eliminating axial clearance between a piston of the cartridge and a piston rod of the drive mechanism.

3. The drug delivery device according to claim 1, wherein the guiding element and the housing are mutually infinitely adjustable.

4. The drug delivery device according to claim 1, wherein the guiding element and the housing are mutually engageable by means of a positive locking means.

5. The drug delivery device according to claim 1, wherein the guiding element and the housing are adhesively connected, mutually bonded and/or welded.

6. The drug delivery device according to claim 1, wherein the housing and the guiding element are mutually connected by means of laser welding.

7. The drug delivery device according to claim 6, wherein the housing is at least partially transparent for a selected laser radiation and wherein the guiding element is adapted to at least partially absorb said laser radiation.

8. The drug delivery device according to claim 7, wherein the housing and the cartridge holder are mutually coupled in axial direction.

9. The drug delivery device according to claim 1, wherein an axial mechanical coupling of the drive mechanism and the housing is exclusively provided by the guiding element.

10. The drug delivery device according to claim 1, further comprising a cartridge filled with the medicinal product.

11. A method of eliminating axial clearance between a cartridge and a drive mechanism of a drug delivery device, wherein:
    the cartridge is disposed in a cartridge holder characterized in that the drive mechanism in its entirety is axially slidingly supported relative to a housing by means of a guiding element axially coupled to the drive mechanism and being slidingly received in the housing,
    wherein during assembly of cartridge holder and housing, the drive mechanism is axially displaced with respect to the housing in response of the drive mechanism operably engaging with the cartridge and
    wherein the drive mechanism is axially fixed with respect to the housing after assembly of housing and cartridge holder.

* * * * *